(12) United States Patent
Li

(10) Patent No.: US 7,636,421 B2
(45) Date of Patent: Dec. 22, 2009

(54) X-RAY IMAGING APPARATUS AND X-RAY CONTROLLING METHOD

(75) Inventor: Huanzhong Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 12/327,963

(22) Filed: Dec. 4, 2008

(65) Prior Publication Data

US 2009/0086897 A1 Apr. 2, 2009

(30) Foreign Application Priority Data

Jul. 12, 2007 (CN) .......................... 2007 1 0305155

(51) Int. Cl.
*H05G 1/42* (2006.01)

(52) U.S. Cl. .......................................... 378/97; 378/42

(58) Field of Classification Search ................... 378/42, 378/51, 62, 98, 98.8, 97, 108, 207
See application file for complete search history.

(56) References Cited

U.S. PATENT DOCUMENTS

| | | | |
|---|---|---|---|
| 4,101,776 A | 7/1978 | Mansfield et al. | |
| 4,573,183 A | 2/1986 | Relihan | |
| 4,703,496 A | 10/1987 | Meccariello et al. | |
| 5,003,572 A | 3/1991 | Meccariello et al. | |
| 5,012,504 A | 4/1991 | McFaul et al. | |
| 5,119,409 A | 6/1992 | Nields et al. | |
| 5,239,567 A | 8/1993 | Loonen | |
| 5,675,624 A | 10/1997 | Relihan et al. | |
| 6,044,127 A | 3/2000 | Van Bree et al. | |
| 6,298,109 B1 * | 10/2001 | Ergun et al. | 378/4 |
| 6,650,729 B2 * | 11/2003 | Braess et al. | 378/108 |
| 2007/0211851 A1 * | 9/2007 | Ogawa | 378/42 |

FOREIGN PATENT DOCUMENTS

JP 08-306498 11/1996

* cited by examiner

*Primary Examiner*—Hoon Song
(74) *Attorney, Agent, or Firm*—Armstrong Teasdale LLP

(57) ABSTRACT

The present invention provides an X-ray imaging apparatus and X-ray controlling method which allows appropriate X-ray control irrespective of the type and position of a subject. The X-ray controller device for controlling the X-ray emission condition of the X-ray emitter device based on the image information of a fluoroscopic image sets within one frame of the fluoroscopic image a plurality of narrow regions and one single wide region encompassing these narrow regions, selects as the formal region, from within the plurality of narrow regions and the wide region, the region in which the subject is assumed to be present, or selects as the formal region the wide region if there is no region in which the subject is assumed to be present, then control the X-ray emission condition of the X-ray emitter device based on the image information in the formal region.

20 Claims, 4 Drawing Sheets

X-RAY IMAGING APPARATUS AND X-RAY CONTROLLING METHOD

CROSS REFERENCE TO RELATED APPLICATIONS

This application claims the benefit of Chinese Patent Application No. 200710305155.6 filed Dec. 12, 2007, which is hereby incorporated by reference in its entirety.

BACKGROUND OF THE INVENTION

The subject matter disclosed herein relates to an X-ray imaging apparatus and X-ray controlling method, more specifically to an X-ray imaging apparatus and X-ray controlling method for controlling the X-ray intensity such that the brightness of fluoroscopic image becomes constant in the R & F (Rad-Fluoro) imaging.

In the R & F imaging, X-ray fluoroscopy is performed in the real time basis. More specifically, while X-ray is continuously emitted to a subject, a plurality of frames of fluoroscopic images is displayed sequentially on a display.

During fluoroscopic imaging, the X-ray intensity control is performed such that the brightness of fluoroscopic images becomes appropriate by device of the automatic brightness control function of an X-ray imaging apparatus. The X-ray intensity control calculates the mean values of brightness information for each of fluoroscopic image frames, then controls X-ray tube voltage and tube current such that the mean values matches with the target value (see for example Japanese Unexamined Patent Publication No. Hei 8(1996)-306498)

BRIEF DESCRIPTION OF THE INVENTION

Calculation of the average value of the brightness information is based on the mean of the brightness information in a fixed region established in an image frame. It is common to set as the fixed region the region corresponding to a coaxial circle 403 in the center of the image 401 based on the signals received from the X-ray acceptance surface of the image intensifier, as shown in FIG. 4. However in the setting of the region established as above, if the subject 405 is placed biased as shown in the figure, the mean values of the brightness information in the fixed region will become higher so that the X-ray to be emitted thereto will be controlled to be decreased, as the result the fluoroscopic images thus obtained will have insufficient brightness with respect to the subject 405 in question.

The problem to be solved by the embodiments described herein is to achieve an X-ray imaging apparatus and X-ray controlling method which can perform the appropriate X-ray control irrespective of the type and placement of the subject.

A first aspect provides an X-ray imaging apparatus, which is used for R & F imaging, comprising: an X-ray emission device for emitting X-ray to a subject; a fluoroscopic image generating device for generating a plurality of sequential frames of fluoroscopic images by the X-ray transmitted through the subject; and an X-ray controller device for controlling the X-ray emission condition of the X-ray emission device based on the image information of the fluoroscopic images, the X-ray controller device establishing a plurality of narrow regions and one single wide region encompassing the narrow regions in one single frame of the fluoroscopic image, selecting as the formal region the region assumed to be the region that the subject is present within the plurality of narrow regions and the wide region, or selecting as the formal region the wide region if there is no region in which the subject is assumed to be present, and controlling the X-ray emission condition of the X-ray emission device based on the image information in the formal region.

A second aspect provides an X-ray imaging apparatus set forth in the first aspect, which is characterized in that: the X-ray controller device establishes a reference which is the region in which the subject is assumed to be present, selects, among the plurality of narrow regions if there are regions which satisfy the reference as well as regions which do not satisfy the reference, the narrow region satisfying the reference as the formal region, and selects, if all of the plurality of narrow regions satisfy the reference or do not satisfy the reference, the wide region as the formal region.

A third aspect provides an X-ray imaging apparatus set forth in the first aspect or in the second aspect described above, which is characterized in that the image information of the narrow regions and wide region is the mean values of pixel information in respective region.

A fourth aspect provides an X-ray imaging apparatus set forth in any one of the first to third aspects described above, which is characterized in that, at switching the formal region, in a first sequential number of frames, if the same formal region is selected then the X-ray controller device switches to the formal region.

A fifth aspect provides an X-ray imaging apparatus set forth in any one of the first to fourth aspects described above, which comprises a display device for displaying the formal region after switching when the formal region is switched.

A sixth aspect provides an X-ray imaging apparatus set forth in any one of the first to fifth aspects described above, which is characterized in that the formal region is selected for a second sequential number of frames.

A seventh aspect provides an X-ray imaging apparatus set forth in any one of the first to sixth aspects described above, which is characterized in that the imaging information in the formal region is the mean values of the pixel information in the region.

An eighth aspect provides an X-ray imaging apparatus set forth in the seventh aspect described above, which is characterized in that the mean value of the formal region is the mean value of the pixel information of the pixels except for the pixels having singular pixel information among pixels of the formal region.

A ninth aspect provides an X-ray imaging apparatus set forth in the seventh aspect described above, which is characterized in that the mean values of the formal region is the mean value of image information of all pixels in the formal region when there are more than the predetermined number of pixels of a singular pixel information, among pixels in the formal region.

A tenth aspect provides an X-ray controlling method comprising an X-ray controller device for controlling an X-ray emission condition of a X-ray emission device based on image information of a fluoroscopic image in an R & F imaging, the X-ray controlling method comprising the steps of: establishing a plurality of narrow regions and a single wide region encompassing the narrow regions in one single frame of the fluoroscopic image; selecting the region in which the subject is assumed to be present within the plurality of narrow regions and the wide region as the formal region or selecting if there is no region in which the subject is assumed to be present, the wide region as the formal region; and controlling the X-ray emission condition of the X-ray emission device based on the image information in the formal region.

An eleventh aspect provides an X-ray controlling method set forth in the tenth aspect described above, comprising the steps of: establishing a reference which is the region in which the subject is assumed to be present; selecting, among the plurality of narrow regions, if there is a region which satisfies the reference along with a region which does not satisfy the reference, the narrow region which satisfies the reference as the formal region; and selecting, if all of the narrow regions satisfy the reference or do not satisfy the reference, the wide region as the formal region.

A twelfth aspect provides an X-ray controlling method set forth in the tenth or eleventh aspect described above, which is characterized in that the image information of the narrow regions and wide region is the mean values of pixel information in respective region.

A thirteenth aspect provides an X-ray controlling method set forth in any one of the tenth to twelfth aspects described above, which is characterized in that, at switching the formal region, in a first sequential number of frames, if the same formal region is selected then the X-ray controller device switches to the formal region.

A fourteenth aspect provides an X-ray controlling method set forth in any one of the tenth to thirteenth aspects described above, which comprises a display device for displaying the formal region after switching when the formal region is switched.

A fifteenth aspect provides an X-ray controlling method set forth in any one of the tenth to fourteenth aspects described above, which is characterized in that the formal region is selected for a second sequential number of frames.

A sixteenth aspect provides an X-ray controlling method set forth in any one of the tenth to fifteenth aspects described above, which is characterized in that the imaging information in the formal region is the mean values of the pixel information in the region.

A seventeenth aspect provides an X-ray controlling method set forth in the sixteenth aspect described above, which is characterized in that the mean value of the formal region is the mean value of the pixel information of the pixels except for the pixels having singular pixel information among pixels of the formal region.

An eighteenth aspect provides an X-ray controlling method set forth in the sixteenth aspect described above, which is characterized in that the mean values of the formal region is the mean value of image information of all pixels in the formal region when there are more than the predetermined number of pixels of the singular pixel information, among pixels in the formal region.

In accordance with the embodiments described herein, an X-ray imaging apparatus and X-ray controlling method are provided, wherein an X-ray controlling device for controlling the X-ray emission condition of the X-ray emission device based on the image information of fluoroscopic images establishes a plurality of narrow regions and a single wide region encompassing the narrow regions in one single frame of the fluoroscopic image, then the region assumed to be the region that the subject is present within the plurality of narrow regions and the wide region is selected as the formal region, whereas if the region that the subject is present is assumed not to be present the wide region is selected as the formal region, then the X-ray emission condition of the X-ray emission device is controlled based on the image information in the formal region. Accordingly, an X-ray imaging apparatus and X-ray controlling method can be realized which can perform the appropriate X-ray control irrespective of the type and placement of the subject.

DETAILED DESCRIPTION OF THE INVENTION

Various embodiments of the invention will be described in greater details herein below with reference to the accompanying drawings. It is to be noted here that the present invention is not to be considered to be limited by the embodiments disclosed below.

Figure 1:
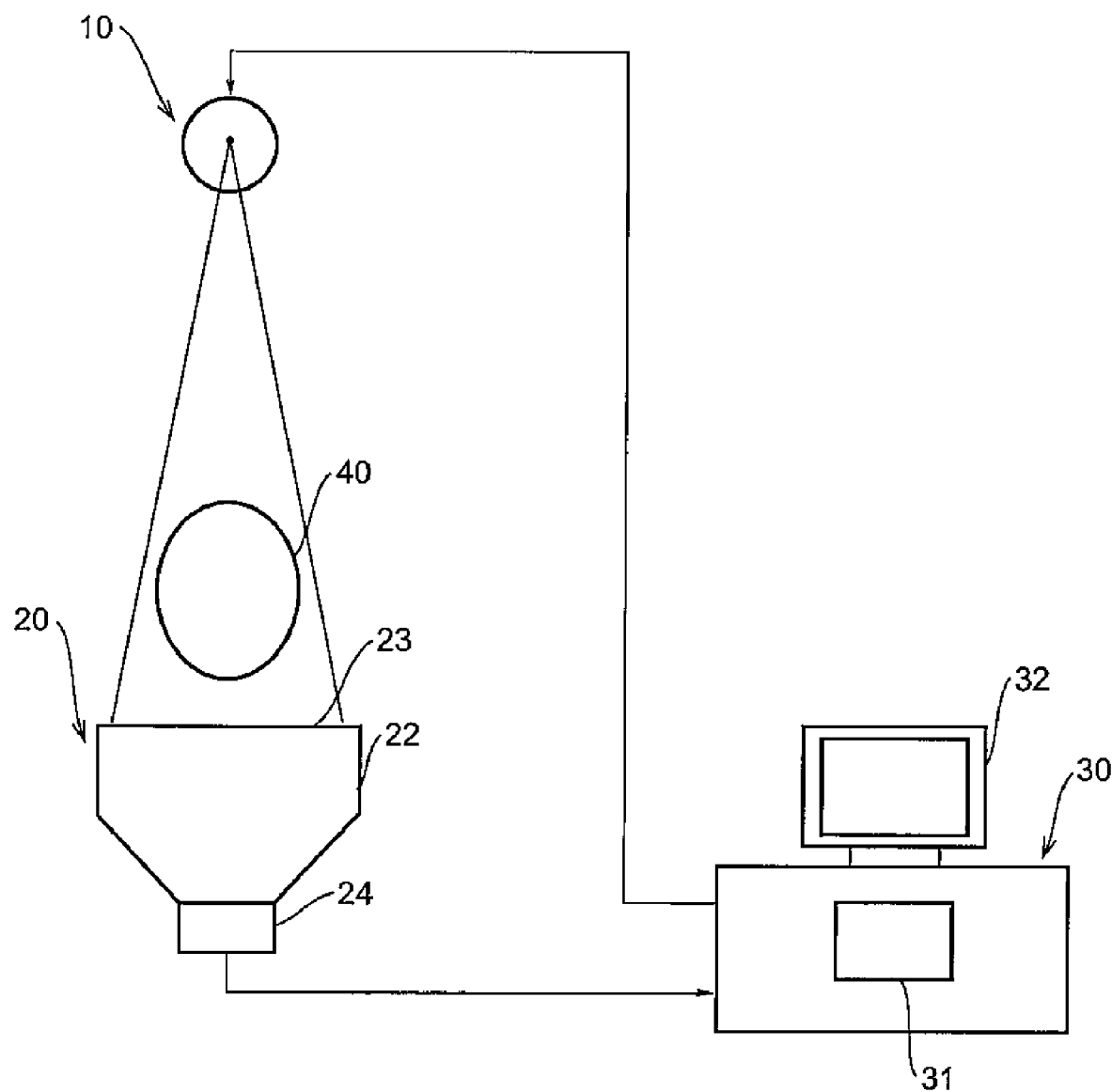
FIG. 1 is a schematic diagram illustrating the arrangement of an X-ray imaging apparatus.

Now referring to FIG. 1, there is shown a schematic diagram of an exemplary X-ray imaging apparatus.

As shown in FIG. 1, the apparatus has an X-ray emitter 10, a fluoroscopic image generator unit 20, and an operator console 30. The X-ray emitter 10 and the X-ray acceptance surface 23 of the fluoroscopic image generator unit 20 are opposed to each other with a space interposed therebetween, in order to image a subject 40 placed therein with the X-ray.

The fluoroscopic image generator unit 20 has an image intensifier 22 and a video camera 24. The image intensifier 22 converts received X-ray into an optical image, which is captured by the video camera 24. The video camera 24 may be a video camera for example having an optical sensor made by a CCD (charge coupled device).

The image captured by the video camera 24 is input to the operator console 30. The operator console 30 displays the input image onto the display 32. On the display 32 the fluoroscopic images during the imaging period will be displayed in the real-time basis.

The operator console 30 also has an X-ray controller unit 31 for controlling the X-ray emitter 10. The control of the X-ray emitter 10 will be done by controlling the X-ray intensity, by feeding back the brightness information of the fluoroscopic image such that the brightness of the fluoroscopic image displayed on the display 32 is appropriate, or constant among frames. The X-ray intensity control is performed by controlling the tube voltage and tube current of the X-ray tube in the X-ray emitter 10.

Figure 2:
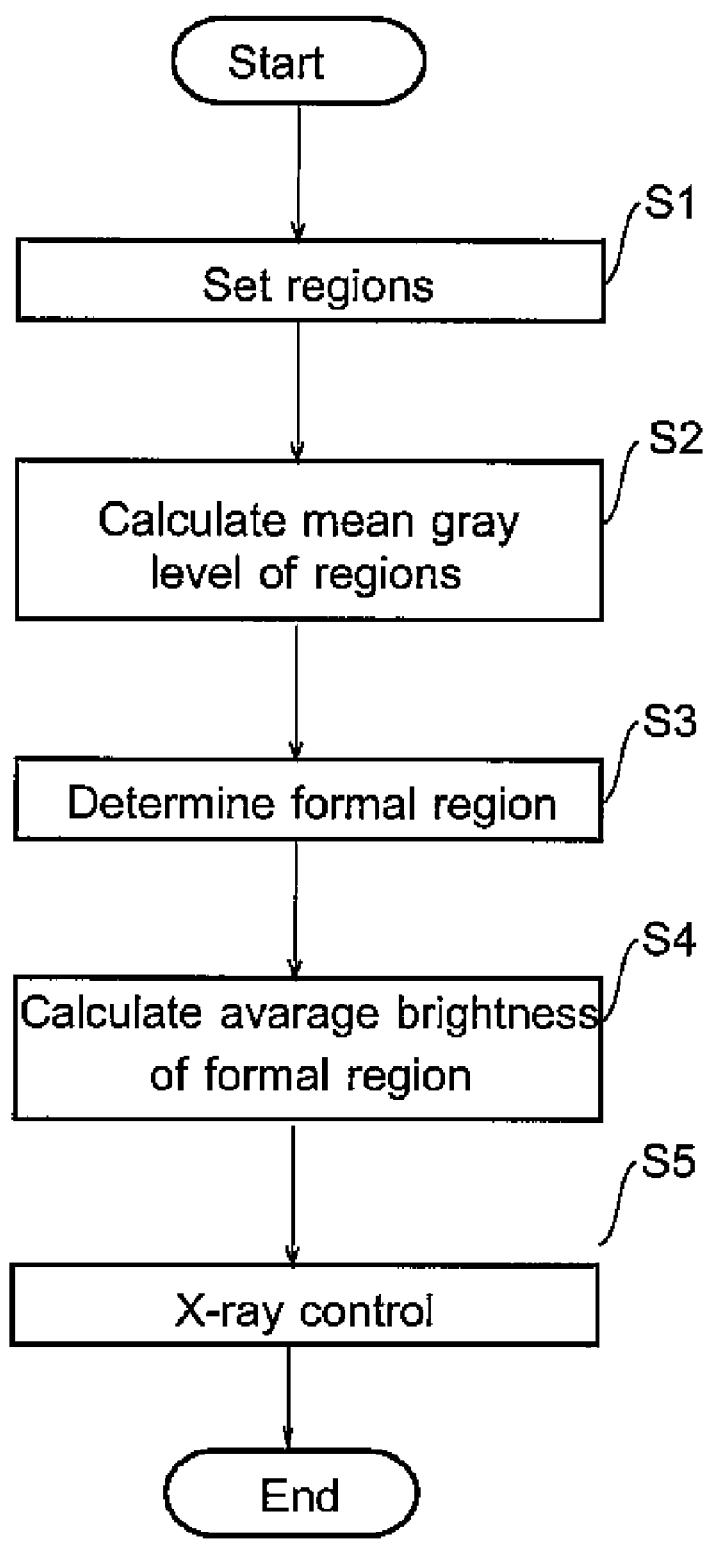
FIG. 2 is a flow chart indicating an exemplary X-ray controlling method in accordance with the exemplary best mode for carrying out the invention.

Now referring to FIG. 2 there is show a flow chart of the operation of the present apparatus. As shown in FIG. 2, in step S1, narrow regions and a wide region are established on the image 5 generated based on the signals received from the X-ray acceptance surface 23 of the image intensifier 22. The region establishment is performed by the user through the operator console 30.

Figure 3:
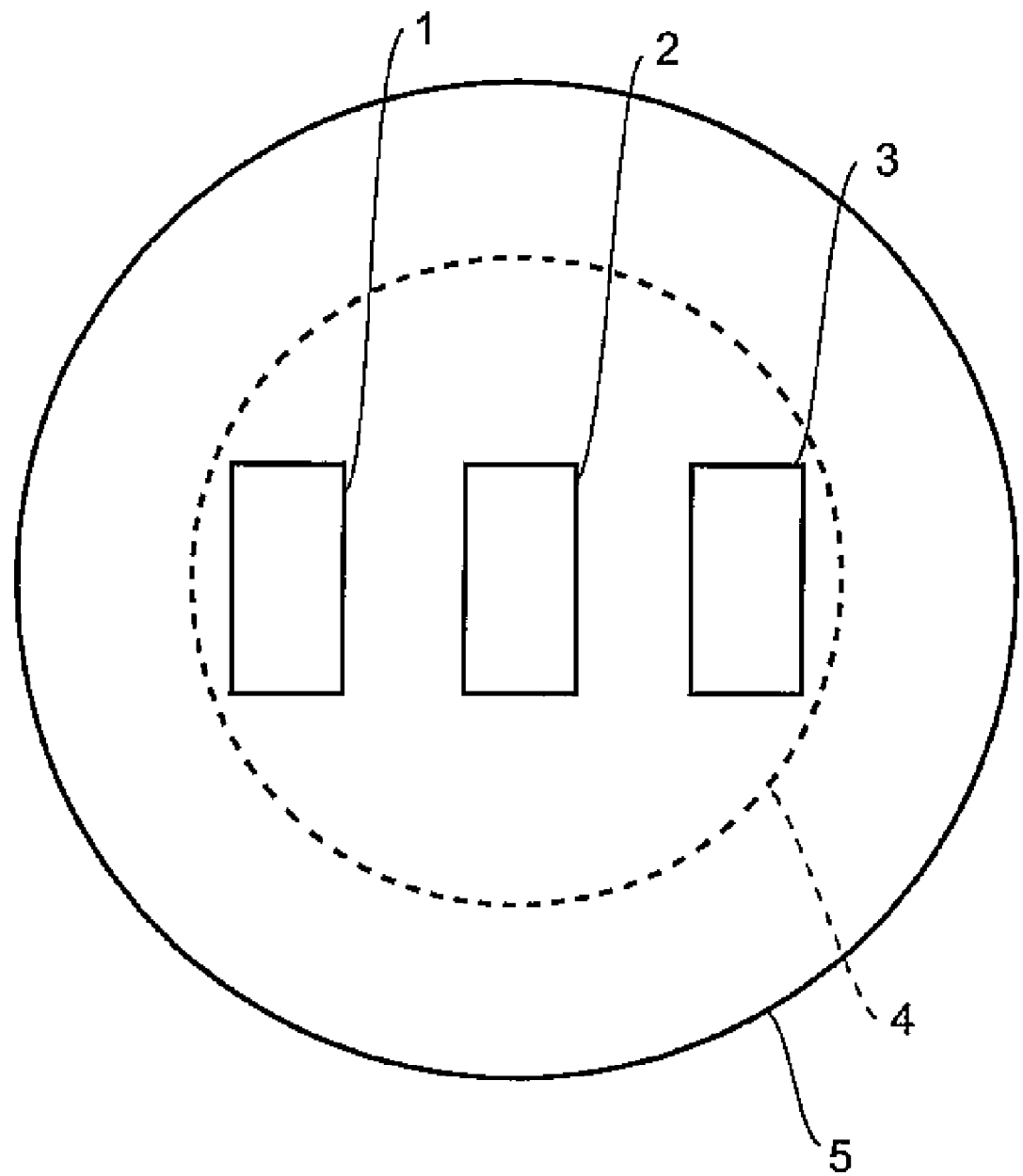
FIG. 3 is a schematic diagram illustrating an example of region setting.

Now referring to FIG. 3 there is shown an example of the establishment of narrow regions and a wide region. As shown in FIG. 3, within one frame of fluoroscopic image, for example four regions of ROIs 1, 2, 3, and 4 are established. These ROIs 1, 2, 3, and 4 are set within the margin of the image 5 based on the signals received from the X-ray acceptance surface 23 of the image intensifier 22.

The ROIs 1, 2, and 3 are relatively narrow regions of rectangles, which are not overlapped. It should be noted here that the shape of ROIs 1, 2, and 3 may not be limited to be rectangular. The size and position may also be set appropriately as desired, provided that ROIs are not overlapped or overlapped each other. The ROIs 1, 2, and 3 are examples of the narrow regions in accordance with the present invention. The ROIs 1, 2, and 3 will be referred to as narrow region ROI herein below.

ROI 4 is a relative wide region of circle encompassing the ROIs 1, 2, and 3. It should be noted here that the shape of the ROI 4 may not be limited to be circular. The size and position may also be set appropriately as desired, provided that it encompasses a plurality of narrow region ROIs. The ROI 4 is an example of the wide region ROI in accordance with the present invention. The ROI 4 will be referred to as a wide region ROI herein below.

In step S2, the mean value of gray level in pixels of these regions is calculated. The calculation of the mean gray level is performed by the operator console 30.

In step S3, a formal region is determined which is the base of brightness information used in the X-ray control as will be described later. The determination of the formal region is performed by the operator console 30. The operator console 30 determines the formal region according to the following expression:

> If Mean_1>Limit1, Mean_2 and Mean_3<Limit1, Select ROI_2+ROI_3 as formal ROI

> If both Mean_1 and Mean_2>Limit1, Mean_3<Limit1, Select ROI_3 as formal ROI

> If Mean_3>Limit1, Mean_2 and Mean_1<Limit1, Select ROI_2+ROI_1 as formal ROI

> If both Mean_3 and Mean_2>Limit1, Mean_1<Limit1, Select ROI_1 as formal ROI

> If Mean_1 and Mean_3>Limit1, Mean_2<Limit1, Select ROI_2 as formal ROI

> If all 3 Mean values>Limit1, Select ROI_4 as formal ROI

> If all 3 Mean values<Limit1, Select ROI_4 as formal ROI                    expression 1 where

Mean_1, Mean_2, Mean_3                    expression 2 are each mean gray level of respective narrow region ROIs 1, 2, and 3, Limit1 is the upper limit value of the gray level, and a subject is assumed to be present if the gray level is less than the upper limit value. Formal ROI is the formal region, determined according to the mean gray level and the relative size relationship between the narrow region ROIs 1, 2, and 3. The upper limit value Limit1 may be set by the user.

The switching of the formal region may be performed when the condition satisfying the above expression is continuously maintained for the predetermined number of frames (first number of frames). A formal ROI determination of good stability may be done thereby. The number of frames is the value settable by the user, and may be set to 6, however the number of frames may be set to any desired number.

As shown by the above expression, if the mean gray level is beyond the upper limit value in one of a plurality of narrow region ROI while is within the limit in others, then the subject is assumed to be present in the narrow region ROI that the mean gray level thereof is not exceeding the limit, so that the narrow region ROI which does not exceed the upper limit value will be determined as the formal region. If the mean gray level in all of a plurality of narrow region ROI is beyond the upper limit value, then the wide region ROI will be determined as the formal region. If the mean gray level in all of a plurality of narrow region ROI is not exceeding the upper limit value then the wide region ROI 4 will be determined as the formal region.

The formal region thus determined is displayed on the display 32 over the fluoroscopic image. By doing this the user may confirm the formal region. The display time of the formal region may be set by the user, for example, it can be set to 1 second, however, the time may also be appropriately set as desired.

Figure 4:
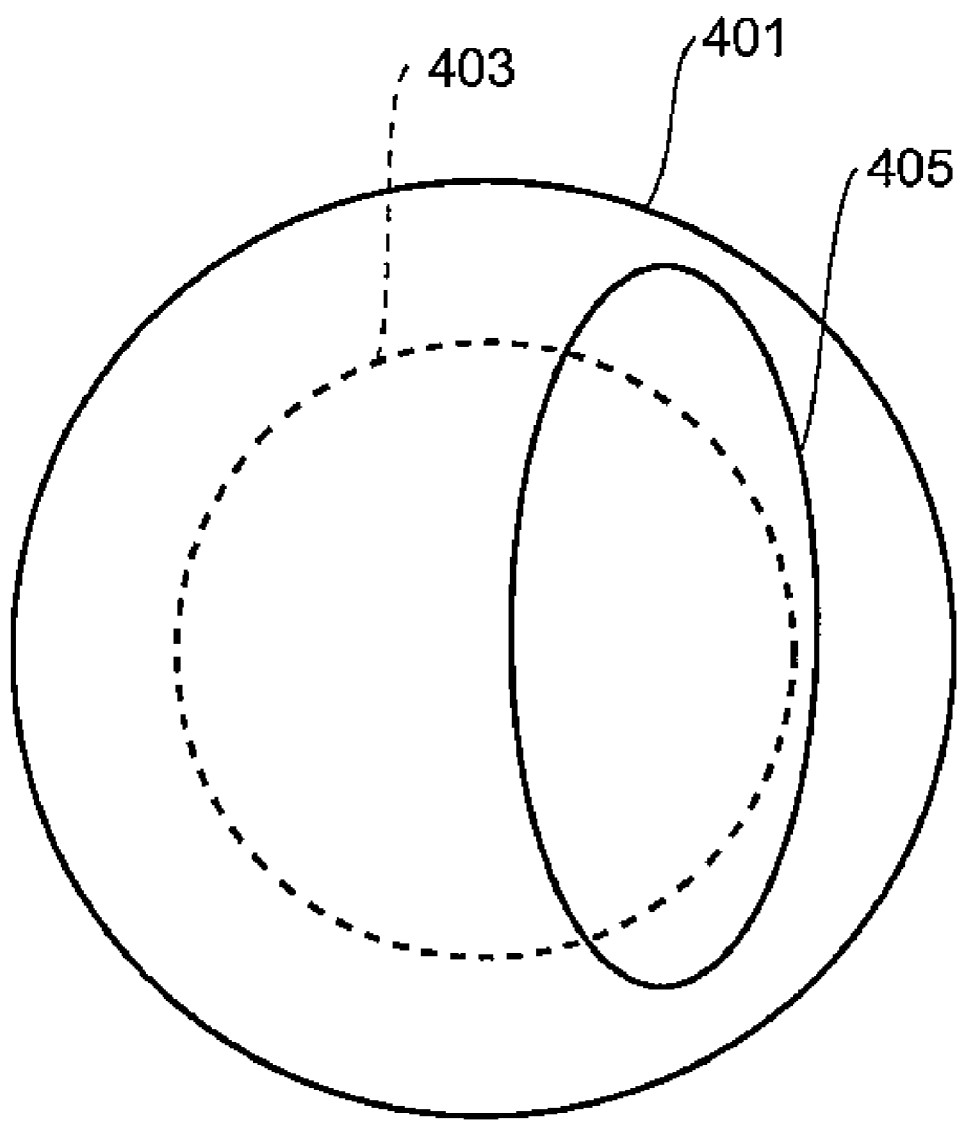
FIG. 4 is a schematic diagram illustrating an example of region setting in accordance with the prior art.

For example, as shown in FIG. 4, if the subject is placed biased to the right side on the acceptance surface of the image intensifier 22, then the narrow region ROI 3 will be determined as the formal region. In other cases, a narrow region ROI or the wide region ROI 4 corresponding to the placement will be determined as the formal region.

The formal region is held at least for the predetermined number of frames (second number of frames). The minimum holding number of frames for the formal region is a value settable by the user, and may be set to 60 frames, however it can be appropriately set as desired.

In step S4, the average brightness of the formal region is calculated. The calculation of the average brightness of the formal region is performed by the operator console 30. The operator console 30 will calculate the average brightness of narrow region ROI 3 in the case shown in FIG. 4. In other cases, the average brightness of the appropriately corresponding narrow region ROI or the wide region ROI will be calculated.

The calculation of the average brightness of the formal region will be performed by excluding any singular values, in other words the anomalies. The exclusion of the abnormal values is done according to the following expression:

> If grey level of the pixel<BlackLimit This pixel shall be abandoned.

Count_b add 1.

> If grey level of the pixel>WhiteLimit This pixel shall be abandoned.

Count_w add 1.                    expression 3

Now BlackLimit is the value indicating the lower limit of the gray level, and WhiteLimit is the value indicating the upper limit of the gray level. These BlackLimit and WhiteLimit are values settable by the user. As shown in the expression 2, the calculation of the average brightness of the formal region is performed by excluding the pixels having gray level below BlackLimit and the pixels having gray level over the WhiteLimit. By doing this the validity of the value of average brightness calculation is improved.

Any excluded pixels are each calculated for the respective case. Count_b and Count_w indicate the count number of the pixels below BlackLimit and the count number of the pixels over WhiteLimit, respectively. These count number are compared with their limits Limit3 and Limit4 as shown in the following expression. If at least any of counts exceeds the limit then the calculation of the average brightness will be performed by using the pixel values of all pixels in the formal region. By doing this the validity of the value of the average brightness calculation is improved.

> If count_b>Limit3, or count_w>Limit4,                    expression 4

Recalculate average brightness and use all pixels.

Recalculate average brightness and use all pixels.

Now limits, Limit3 and Limit4, are values settable by the user.

In step S5 X-ray is controlled. The X-ray control is performed by the operator console 30. The operator console 30 controls the X-ray intensity such that the average brightness of the formal region determined as above coincides with the target value. Since the validity of the average brightness of the formal region is enough higher, the X-ray control will be performed appropriately.

In the case as shown in FIG. 4, the operator console 30 will control the X-ray intensity such that the average brightness of the narrow region ROI 3 coincides with the target value. In other cases it controls the X-ray intensity such that the average brightness of the either corresponding narrow region ROI or the wide region ROI 4 coincides with the target value. By doing this the brightness of the fluoroscopic image corresponds to the shape and position of the subject.

I claim:

1. An X-ray imaging apparatus configured for use in Rad-Flouro (R&F) imaging, said X-ray imaging apparatus comprising:
    an X-ray emission device configured to emit X-ray to a subject;
    a fluoroscopic image generating device configured to generate a plurality of sequential frames of fluoroscopic images by the X-ray transmitted through the subject; and
    an X-ray controller device configured to control an the X-ray emission condition of said X-ray emission device based on image information of the fluoroscopic images, said X-ray controller device further configured to establish a plurality of narrow regions and one single wide region encompassing the narrow regions, to select one of a region assumed to be the region that the subject is present within the plurality of narrow regions and the wide region as a formal region, and the wide region as the formal region if there is no region in which the subject is assumed to be present, and to control the X-ray emission condition of said X-ray emission device based on the image information in the formal region.

2. An X-ray imaging apparatus according to claim 1, wherein said X-ray controller device is configured to:
    establish a reference which is the region in which the subject is assumed to be present;
    select, among the plurality of narrow regions if there regions which satisfy the reference as well as regions which do not satisfy the reference, the narrow region satisfying the reference as the formal region; and
    select, if all of the narrow regions satisfy the reference or do not satisfy the reference, the wide region as the formal region.

3. An X-ray imaging apparatus according to claim 1, wherein the image information of the narrow regions and wide region is the mean values of pixel information in each respective region.

4. An X-ray imaging apparatus according to claim 1, wherein said X-ray controller device is configured to switch to the formal region in a first sequential number of frames, if the same formal region is selected.

5. An X-ray imaging apparatus according to claim 1, further comprising a display device configured to display the formal region after the formal region is switched.

6. An X-ray imaging apparatus according to claim 1, wherein the formal region is selected for a second sequential number of frames.

7. An X-ray imaging apparatus according to claim 1, wherein the imaging information in the formal region is a mean value of the pixel information in the formal region.

8. An X-ray imaging apparatus according to claim 7, wherein the mean value of the pixel information in the formal region is the mean value of the pixel information of all pixels in the formal region except for the pixels having singular pixel information.

9. An X-ray imaging apparatus according to claim 7, wherein the mean value of the pixel information in the formal region is the mean value of image information of all pixels in the formal region when there are more than a predetermined number of pixels of having singular pixel information among the pixels in the formal region.

10. An X-ray controlling method for use by an X-ray controller device for controlling an X-ray emission condition of an X-ray emitter device based on image information of a fluoroscopic image, said X-ray controlling method comprising:
    establishing a plurality of narrow regions and a single wide region encompassing the narrow regions in one single frame of the fluoroscopic image;
    one of selecting a region in which a subject is assumed to be present within the plurality of narrow regions and the wide region as a formal region, and selecting if there is no region in which the subject is assumed to be present, the wide region as the formal region; and
    controlling the X-ray emission condition of the X-ray emission device based on image information in the formal region.

11. An X-ray controlling method according to claim 10, further comprising:
    establishing a reference which is the region in which the subject is assumed to be present;
    selecting the narrow region which satisfies the reference as the formal region, if there is a region which satisfies the reference and a region which does not satisfy the reference; and
    selecting the wide region as the formal region, if all of the plurality of narrow regions one of satisfy the reference and do not satisfy the reference.

12. An X-ray controlling method according to claim 10, wherein
    the image information of the narrow regions and the wide region is the mean values of pixel information in respective region.

13. An X-ray controlling method according to claim 10, further comprising switching the formal region, in a first sequential number of frames, if the same formal region is selected.

14. An X-ray controlling method according to claim 13, further comprising displaying the formal region when the formal region is switched.

15. An X-ray controlling method according to claim 10, further comprising selecting the formal region for a second sequential number of frames.

16. An X-ray controlling method according to claim 10, further comprising determining the imaging information in the formal region, wherein the image information is a mean value of the pixel information in the region.

17. An X-ray controlling method according to claim 16, wherein determining the image information in the formal region comprises determining the mean value of the pixel information of all pixels in the formal region except for pixels having singular pixel information.

18. An X-ray controlling method according to claim 16, wherein determining the image information in the formal region comprises determining the mean value of image information of all pixels in the formal region when there are more than a predetermined number of pixels of having singular pixel information among the pixels in the formal region.

19. An X-ray controller device coupled to an X-ray emission device and a fluoroscopic image generating device of an X-ray imaging apparatus, said X-ray controller device configured to:
- control an the X-ray emission condition of the X-ray emission device based on image information of fluoroscopic images generated by the fluoroscopic image generating device;
- establish a plurality of narrow regions and one single wide region encompassing the narrow regions;
- select one of a region assumed to be the region that the subject is present within the plurality of narrow regions and the wide region as a formal region, and the wide region as the formal region if there is no region in which the subject is assumed to be present; and
- control the X-ray emission condition of said X-ray emission device based on the image information in the formal region.

20. An X-ray controller device according to claim 19, said X-ray controller device further configured to:
- establish a reference which is the region in which the subject is assumed to be present;
- select, among the plurality of narrow regions if there regions which satisfy the reference as well as regions which do not satisfy the reference, the narrow region satisfying the reference as the formal region; and
- select, if all of the narrow regions satisfy the reference or do not satisfy the reference, the wide region as the formal region.

* * * * *